United States Patent
Nakano et al.

(10) Patent No.: US 10,760,050 B2
(45) Date of Patent: Sep. 1, 2020

(54) METHOD FOR PRODUCING RETINAL PIGMENT EPITHELIAL CELLS

(71) Applicants: SUMITOMO CHEMICAL COMPANY, LIMITED, Tokyo (JP); RIKEN, Wako-shi, Saitama (JP)

(72) Inventors: Tokushige Nakano, Osaka (JP); Yoshiki Sasai, Kobe (JP); Chikafumi Ozone, Wako (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 210 days.

(21) Appl. No.: 15/035,966

(22) PCT Filed: Oct. 2, 2014

(86) PCT No.: PCT/JP2014/076471
§ 371 (c)(1),
(2) Date: May 11, 2016

(87) PCT Pub. No.: WO2015/068505
PCT Pub. Date: May 14, 2015

(65) Prior Publication Data
US 2016/0264936 A1    Sep. 15, 2016

(30) Foreign Application Priority Data

Nov. 11, 2013 (JP) ................................ 2013-232795

(51) Int. Cl.
*C12N 5/079* (2010.01)
*A61L 27/38* (2006.01)
*C12N 5/0793* (2010.01)
*A61K 35/30* (2015.01)
*A61K 35/545* (2015.01)

(52) U.S. Cl.
CPC ............ *C12N 5/0621* (2013.01); *A61K 35/30* (2013.01); *A61L 27/3813* (2013.01); *A61L 27/3834* (2013.01); *A61L 27/3895* (2013.01); *C12N 5/062* (2013.01); *A61K 35/545* (2013.01); *A61L 2430/16* (2013.01); *C12N 2501/113* (2013.01); *C12N 2501/155* (2013.01); *C12N 2501/41* (2013.01); *C12N 2501/415* (2013.01); *C12N 2501/727* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 2011/0027333 A1 | 2/2011 | Idelson et al. | |
| 2011/0223140 A1 | 9/2011 | Park et al. | |
| 2014/0057281 A1 | 2/2014 | Takahashi et al. | |
| 2014/0308743 A1 | 10/2014 | Sasai et al. | |
| 2014/0341864 A1 | 11/2014 | Nakano et al. | |
| 2015/0118749 A1 | 4/2015 | Idelson et al. | |
| 2015/0125506 A1 | 5/2015 | Idelson et al. | |
| 2015/0175964 A1* | 6/2015 | Clegg | C12N 5/0621 435/377 |
| 2016/0251616 A1 | 9/2016 | Nakano et al. | |

FOREIGN PATENT DOCUMENTS

| | | |
|---|---|---|
| JP | 2010-524457 A | 7/2010 |
| JP | 2013-128474 A | 7/2013 |
| WO | WO 2011/028524 A1 | 3/2011 |
| WO | WO 2011/043591 A2 | 4/2011 |
| WO | WO 2011/055855 A1 | 5/2011 |
| WO | WO 2012/115244 A1 | 8/2012 |
| WO | WO 2012/173207 A1 | 12/2012 |

(Continued)

OTHER PUBLICATIONS

Osakada et al., Toward the generation of rod and cone photoreceptors from mouse, monkey and human embryonic stem cells, Nature Biotechnology, vol. 26, No. 2, Feb. 2008, pp. 215-224.*
Buchholz et al., Stem Cells Translational Medicine, 2013; 2:384-393 (Year: 2013).*
Idelson et al., Cell Stem Cell 5, 396-408, Oct. 2, 2009 (Year: 2009).*
Idelson et al., "Directed Differentiation of Human Embryonic Stem Cells into Functional Retinal Pigment Epithelium Cells," *Cell Stem Cell*, 5(4): 396-408 (2009).
Nakano et al., "Self-Formation of Optic Cups and Storable Stratified Neural Retina from Human ESCs," *Cell Stem Cell*, 10(6): 771-785 (2012).

(Continued)

*Primary Examiner* — Scott Long
*Assistant Examiner* — Evelyn Y Pyla
(74) *Attorney, Agent, or Firm* — Leydig, Voit & Mayer, Ltd.

(57) ABSTRACT

The present invention provides
a method for producing a retinal pigment epithelial cell, including
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and
(3) a third step of subjecting the aggregate formed in step (2) to floating culture in a serum-free medium or serum-containing medium each being free of a substance acting on the Sonic hedgehog signal transduction pathway and a substance acting on the BMP signal transduction pathway and containing a substance acting on the Wnt signal pathway, thereby obtaining an aggregate containing retinal pigment epithelial cell.

20 Claims, 2 Drawing Sheets

(56) References Cited

FOREIGN PATENT DOCUMENTS

| WO | WO 2013/065763 A1 | 5/2013 |
| WO | WO 2015/025967 A1 | 2/2015 |

OTHER PUBLICATIONS

Vaajasaari et al., "Toward the defined and xeno-free differentiation of functional human pluripotent stem cell-derived retinal pigment epithelial cells," *Mol. Vis.*, 17: 558-575 (2011).

European Patent Office, Extended European Search Report in European Patent Application No. 14860084.4 (dated May 3, 2017).

Japanese Patent Office, International Search Report in International Patent Application No. PCT/JP2014/076471 (dated Jan. 13, 2015).

Japanese Patent Office, Written Opinion of the International Searching Authority in International Patent Application No. PCT/JP2014/076471 (dated Jan. 13, 2015).

Bharti et al., "The new paradigm: retinal pigment epithelium cells generated from embryonic or induced pluripotent stem cells," *Pigment Cell Melanoma Res.*, 24(1): 21-34 (2010).

Borooah et al., "Using human induced pluripotent stem cells to treat retinal disease," *Prog. Retin. Eye Res.*, 37: 163-181 (2013).

Osakada et al., "Stepwise differentiation of pluripotent stem cells into retinal cells," *Nat. Protoc.*, 4(6): 811-824 (2009).

Rowland et al., "Pluripotent Human Stem Cells for the Treatment of Retinal Disease," *J. Cell Physiol.*, 227(2): 457-466 (2011).

Yang, "Roles of cell-extrinsic growth factors in vertebrate eye pattern formation and retinogenesis," *Semin. Cell Dev. Biol.*, 15(1): 91-103 (2004).

Intellectual Property Office of Singapore, Search Report in Singaporean Patent Application 11201603719Q (dated Oct. 2, 2017).

Attisano et al., "Signal Transduction by the TGF-βSuperfamily," *Science*, 296(5573): 1646-1647 (2002).

Itoh et al., "Roles of TGF-13 family signals in the fate determination of pluripotent stem cells," *Semin. Cell Dev. Biol.*, 32: 98-106 (2014).

\* cited by examiner

METHOD FOR PRODUCING RETINAL PIGMENT EPITHELIAL CELLS

CROSS-REFERENCE TO RELATED APPLICATIONS

This patent application is the U.S. national phase of International Patent Application No. PCT/JP2014/076471, filed Oct. 2, 2014, which claims the benefit of Japanese Patent Application No. 2013-232795, filed on Nov. 11, 2013, which are incorporated by reference in their entireties herein.

TECHNICAL FIELD

The present invention relates to a method for producing retinal pigment epithelial cells and others.

BACKGROUND ART

A report on the production of retinal pigment epithelial cells using pluripotent stem cells is known (non-patent document 1). Methods of obtaining a retinal pigment epithelial cell by forming a homogeneous aggregate of pluripotent stem cells in a serum-free medium containing a substance inhibiting the Wnt signal pathway, subjecting them to floating culture in the presence of a basement membrane preparation, then to floating culture in a serum-containing medium, and to floating culture in a serum-free medium or serum-containing medium containing a substance acting on the Wnt signal pathway and free of a substance acting on the Sonic hedgehog signal pathway (non-patent document 2 and patent document 1) are shown.

DOCUMENT LIST

Patent Document patent document 1: WO 2013/077425

Non-Patent Documents non-patent document 1: Cell Stem Cell, 5, 396-408 (2009)
non-patent document 2: Cell Stem Cell, 10(6), 771-785 (2012)

SUMMARY OF THE INVENTION

Problems to be Solved by the Invention

The development of a method for producing a retinal pigment epithelial cell from a pluripotent stem cell has been desired.

Means of Solving the Problems

The present invention provides a method for producing retinal pigment epithelial cells or a retinal pigment epithelial cell sheet from pluripotent stem cells, and so on.

That is, the present invention provides:
[1] a method for producing a retinal pigment epithelial cell, comprising
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and
(3) a third step of subjecting the aggregate obtained in step (2) to floating culture in a serum-free medium or serum-containing medium each being free of a substance acting on the Sonic hedgehog signal transduction pathway and a substance acting on the BMP signal transduction pathway and containing a substance acting on the Wnt signal pathway, thereby obtaining an aggregate containing retinal pigment epithelial cell (hereinafter sometimes referred to as production method 1 of the present invention);
[2] a method for producing a retinal pigment epithelial cell sheet, comprising
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells,
(3) a third step of subjecting the aggregate obtained in step (2) to floating culture in a serum-free medium or serum-containing medium each being free of a substance acting on the Sonic hedgehog signal transduction pathway and a substance acting on the BMP signal transduction pathway and containing a substance acting on the Wnt signal pathway, thereby obtaining an aggregate containing retinal pigment epithelial cell, and
(4) a fourth step of dispersing the aggregate obtained in step (3) and subjecting the resulting cells to adhesion culture (hereinafter sometimes referred to as production method 2 of the present invention);
[3] the production method of the aforementioned [2], wherein the adhesion culture is performed in the presence of a serum replacement in the step (4);
[4] the production method of the aforementioned [2] or [3], wherein the adhesion culture is performed in the presence of a ROCK inhibitory substance, in the step (4);
[5] the production method of any of the aforementioned [2] to [4], wherein the adhesion culture is performed in a serum-free medium or serum-containing medium further comprising one or more substances selected from the group consisting of a substance acting on the Wnt signal pathway, a substance inhibiting the FGF signal pathway, a substance acting on the Activin signal pathway and a substance acting on the BMP signal transduction pathway, in the step (4);
[6] the production method of any of the aforementioned [2] to [5], wherein the adhesion culture is performed on a culture vessel material having a surface treated with a culture substrate, in the step (4);
[7] the production method of the aforementioned [6], wherein the culture substrate is a synthetic culture substrate;
[8] the production method of the aforementioned [6], wherein the culture substrate is laminin;
[9] the production method of any of the aforementioned [1] to [8], wherein the pluripotent stem cells are primate pluripotent stem cells;
[10] the production method of any of the aforementioned [1] to [9], wherein the pluripotent stem cells are human pluripotent stem cells;

[11] the method of any of the aforementioned [1] to [10], wherein the step (1) and step (2) are performed in the presence of a serum replacement;

[12] the method of any of the aforementioned [1] to [11], wherein the floating culture is performed in the absence of a basement membrane preparation;

[13] the method of any of the aforementioned [1] to [12], wherein the substance acting on the BMP signal transduction pathway is one or more proteins selected from the group consisting of BMP2, BMP4, BMP7 and GDF7;

[14] the method of any of the aforementioned [1] to [13], wherein the serum-free medium or serum-containing medium each being free of a substance acting on the Sonic hedgehog signal transduction pathway and a substance acting on the BMP signal transduction pathway and containing a substance acting on the Wnt signal pathway in step (2) further comprises a substance inhibiting the FGF signal pathway;

[15] a reagent for evaluating toxicity or drug efficacy, comprising a retinal pigment epithelial cell or a retinal pigment epithelial cell sheet, which is produced by the method of any of the aforementioned [1] to [14];

[16] a method of evaluating toxicity or drug efficacy of a test substance, comprising bringing a retinal pigment epithelial cell or a retinal pigment epithelial cell sheet produced by the method of any of the aforementioned [1] to [14], into contact with the test substance, and examining the influence of the substance on the cell or cell sheet;

[17] a therapeutic agent for a disease due to a disorder of a retinal tissue, comprising a retinal pigment epithelial cell or retinal pigment epithelial cell sheet produced by the method of any of the aforementioned [1] to [14];

[18] a method of treating a disease due to a disorder of a retinal tissue, comprising transplanting an effective amount of a retinal pigment epithelial cell or retinal pigment epithelial cell sheet produced by the method of any of the aforementioned [1] to [14], to a subject in need of the transplantation; and

[19] a retinal pigment epithelial cell or a retinal pigment epithelial cell sheet produced by the method of any of the aforementioned [1] to [14], for use in the treatment of a disease due to a disorder of a retinal tissue; and the like.

Effect of the Invention

According to the production method of the present invention, a retinal pigment epithelial cell or retinal pigment epithelial cell sheet can be produced with high efficiency. In the production method of the present invention, since a retinal pigment epithelial cell or retinal pigment epithelial cell sheet can be obtained by floating culture of an aggregate without adding a basement membrane preparation to a medium, namely, in the absence of a basement membrane preparation, the risk of contamination of the obtained cell or cell sheet with a component derived from a heterologous species is reduced. According to the production method of the present invention, a retinal pigment epithelial cell or retinal pigment epithelial cell sheet can be efficiently provided for the purpose of toxicity or efficacy evaluation of a chemical substance etc., transplantation treatment and so on.

DESCRIPTION OF EMBODIMENTS

Figure 1:
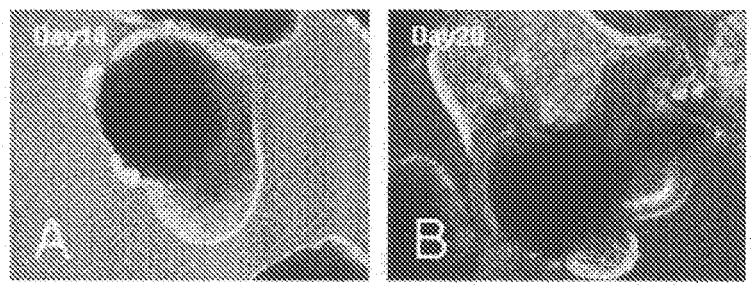
FIG. 1 shows bright field image (A) at day 18 of the floating culture of aggregates, derived from human embryonic stem cells, floating cultured in a medium supplemented with BMP4 on day 3 of floating culture, and bright field image (B) at day 20 of the floating culture of aggregates, derived from human embryonic stem cells, floating cultured in a medium supplemented with BMP4 on day 3 of floating culture and floating cultured in a medium free of BMP4 and containing CHIR99021 from day 18 of floating culture.

Mode(s) for carrying out the present invention is(are) explained in detail below.

The "floating culture" in the present invention means cultivating under conditions prohibiting adhesion of cell or cell mass to a cell culture vessel material etc.

The culture vessel to be used in floating culture is not particularly limited as long as it enables "floating culture", and those of ordinary skill in the art can appropriately determine same. Examples of such culture vessel include flask, tissue culture flask, dish, petri dish, tissue culture dish, multidish, microplate, microwell plate, micropore, multiplate, multiwell plate, chamber slide, schale, tube, tray, culture bag, and roller bottle. Since these culture vessels are used for floating culture, they are preferably cell non-adhesive. As a cell non-adhesive vessel, one having its surface not artificially treated to improve cell adhesiveness (e.g., coating treatment with extracellular matrix, etc.) and so on can be used.

The medium to be generally used in the present invention can be prepared from a medium used for culture of animal cell as a basal medium. Examples of the basal medium include those that can be used for culturing animal cells, such as BME medium, BGJb medium, CMRL1066 medium, Glasgow MEM medium, Improved MEM Zinc Option medium, IMDM medium, Medium199 medium, Eagle MEM medium, αMEM medium, DMEM medium, F-12 medium, Ham's medium, RPMI1640 medium, Fischer's medium, and mixed medium thereof.

The "serum-free medium" in the present invention means a medium free of unadjusted or unpurified serum. In the present invention, a medium containing purified blood-derived components and animal tissue-derived components (e.g., growth factor) is considered to be a serum-free medium unless unadjusted or unpurified serum is contained therein.

The serum-free medium may contain a serum replacement. Examples of the serum replacement include those appropriately containing, for example, albumin, transferrin, fatty acid, collagen precursor, trace element, 2-mercaptoethanol or 3' thiolglycerol, an equivalent thereof and so on. Such serum replacement can be prepared by, for example, the method described in WO98/30679. In addition, the serum replacement can be a commercially available product. Examples of such commercially available serum replacement include KNOCKOUT™ Serum Replacement (manufactured by Invitrogen: hereinafter sometimes referred to as KSR), Chemically defined lipid concentrate (manufactured by Gibco), and GLUTAMAX™ supplement (manufactured by Gibco).

The serum-free medium to be used for floating culture may contain fatty acid or lipid, amino acid (e.g., non-essential amino acid), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 1-about 20%) of commercially available KSR can be used as the serum-free medium (e.g., medium obtained by adding 10% KSR and 450 μM 1-monothioglycerol to a 1:1 mixture of F-12 medium and IMDM medium).

The "serum-containing medium" in the present invention means a medium containing unadjusted or unpurified serum. The medium may contain fatty acid or lipid, amino acid (e.g., non-essential amino acid), vitamin, growth factor, cytokine, antioxidant, 2-mercaptoethanol, 1-monothioglycerol, pyruvic acid, buffering agent, inorganic salts and so on.

The "basement membrane preparation" in the present invention refers to one containing basement membrane-constituting components having a function to control cell form, differentiation, growth, motility, expression of function and so on which are similar to those of epithelial cell, when intended cells capable of forming a basement membrane are plated thereon and cultured. Here, the "basement membrane constituting component" refers to an extracellular matrix molecule in the form of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of preferable basement membrane preparation include products commercially available as basement membrane product (e.g., MATRIGEL™ extracellular matrix (manufactured by Beckton Dickinson: hereinafter sometimes to be referred to as Matrigel)), and extracellular matrix molecules known as basement membrane components (e.g., laminin, type IV collagen, heparan sulfate proteoglycan, entactin and so on).

MATRIGEL™ extracellular matrix is a basement membrane product extracted from Engelbreth Holm Swam (EHS) mouse sarcoma. The main component of MATRIGEL™ extracellular matrix is type IV collagen, laminin, heparan sulfate proteoglycan, and entactin. In addition to these, TGF-β, fibroblast growth factor (FGF), tissue plasminogen activator, and a growth factor naturally produced by EHS tumor are contained. The "growth factor reduced product" of MATRIGEL™ extracellular matrix has a lower growth factor concentration than common MATRIGEL™ extracellular matrix, and the standard concentration thereof is <0.5 ng/ml for EGF, <0.2 ng/ml for NGF, <5 pg/ml for PDGF, 5 ng/ml for IGF-1, and 1.7 ng/ml for TGF-β.

The "medium containing substance X" in the present invention means a medium supplemented with an exogenous substance X or a medium containing an exogenous substance X, and the "medium free of substance X" means a medium not supplemented with an exogenous substance X or a medium not containing an exogenous substance X. Here, the "exogenous substance X" means a substance X exogenous to a cell or tissue to be cultured in the medium, and an endogenous substance X produced by the cell or tissue is not included therein.

For example, a "medium containing a substance acting on the BMP signal transduction pathway" is a medium supplemented with an exogenous substance acting on the BMP signal transduction pathway or a medium containing an exogenous substance acting on the BMP signal transduction pathway. A "medium free of a substance acting on the Sonic hedgehog signal transduction pathway" is a medium not supplemented with an exogenous substance acting on the Sonic hedgehog signal transduction pathway or a medium not containing an exogenous substance acting on the Sonic hedgehog signal transduction pathway.

The "primates" in the present invention mean mammals belonging to primate. Examples of the primates include Strepsirrhini such as lemur, loris, and Tsubai, and Haplorhini such as monkey, anthropoid ape, and human.

In the present invention, the "stem cell" refers to a cell that maintains the same differentiation capacity even after cell division, which can contribute to the regeneration of a tissue thereof when the tissue is injured. Here, the stem cell may be an embryonic stem cell (hereinafter sometimes to be referred to as ES cell) or a tissue stem cell (also called tissular stem cell, tissue-specific stem cell or somatic stem cell), or an artificial pluripotent stem cell (iPS cell: induced pluripotent stem cell). As is appreciated from the fact that the above-mentioned stem cell-derived tissue cell can regenerate a tissue, it is known that the stem cell can differentiate into a normal cell close to one in a living body.

Stem cells are available from given organizations, or a commercially available product can also be purchased. For example, human embryonic stem cells, KhES-1, KhES-2 and KhES-3, are available from Kyoto University's Institute for Frontier Medical Sciences. EB5 cell is available from RIKEN, and D3 cell line is available from ATCC, each of which is a mouse embryonic stem cell.

Stem cells can be maintained by culturing according to a method known per se. For example, human stem cells can be maintained by culturing in a medium supplemented with KNOCKOUT™ Serum Replacement (Invitrogen). Mouse stem cells can be maintained by adding fetal bovine serum (FCS) and Leukemia Inhibitory Factor (LIF) and culturing without feeder cells.

In the present invention, the "pluripotent stem cell" refers to a stem cell that can be cultured in vitro and has an ability to differentiate into any cell (triploblast (ectoderm, mesoderm, endoderm)-derived tissue) constituting a living body except for placenta (pluripotency), and an embryonic stem cell (ES cell) is included in the pluripotent stem cell. The "pluripotent stem cell" is obtained from fertilized egg, clone embryo, reproductive stem cell, and stem cell in a tissue. A cell having artificial differentiation pluripotency similar to that of embryonic stem cells, after introducing several kinds of genes into a somatic cell (also called artificial pluripotent stem cell) is also included in the pluripotent stem cell. Pluripotent stem cell can be produced by a method known per se. Examples of the production method include the methods described in Cell, 2007, 131(5) pp. 861-872 and Cell, 2006, 126(4) pp. 663-676.

In the present invention, the "embryonic stem cell (ES cell)" refers to a stem cell having a self replication ability and multipotency (particularly, "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

In the present invention, the "artificial pluripotent stem cell" refers to a cell induced to have multipotency by directly reprogramming a differentiated cell such as fibroblast etc. by the expression of several kinds of genes such as Oct3/4, Sox2, Klf4, and Myc, which was established by Yamanaka et al. in mouse cell in 2006 (Cell. 2006, 126(4), pp. 663-676). In 2007, induced pluripotent stem cell was also established in human fibroblast, and has multipotency similar to that of embryonic stem cells (Cell, 2007, 131(5) pp. 861-872; Science, 2007, 318(5858) pp. 1917-1920; Nat. Biotechnol., 2008, 26(1) pp. 101-106).

A genetically-modified pluripotent stem cell can be produced, for example, using a homologous recombination technique. Examples of the gene on the chromosome to be modified include a cell marker gene, a histocompatibility antigen gene, a gene related to a disease due to a disorder of nerve system cell and so on. A target gene on the chromosome can be modified by the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Bio Manual series 8, gene targeting, Production of mutant mouse using ES cells, YODOSHA CO., LTD. (1995) and so on.

To be specific, for example, the genomic gene of a target gene to be modified (e.g., cell marker gene, histocompatibility antigen gene, disease-related gene and so on) is isolated, and a target vector used for homologous recombination of the target gene is produced using the isolated genomic gene. The produced target vector is introduced into stem cells, and cells showing homologous recombination between the target gene and the target vector are selected, whereby stem cells having modified gene on the chromosome can be produced.

As a method for isolating the genomic gene of the target gene, known methods described in Molecular Cloning, A Laboratory Manual, Second Edition, Cold Spring Harbor Laboratory Press (1989), Current Protocols in Molecular Biology, John Wiley & Sons (1987-1997) and so on can be mentioned. Moreover, the genomic gene of the target gene can be isolated using genomic DNA library screening system (manufactured by Genome Systems), Universal GenomeWalker Kits (manufactured by CLONTECH) and so on.

A target vector used for homologous recombination of the target gene can be produced, and a homologous recombinant can be efficiently selected according to the methods described in Gene Targeting, A Practical Approach, IRL Press at Oxford University Press (1993); Bio Manual series 8, gene targeting, Production of mutant mouse using ES cells, YODOSHA CO., LTD. (1995) and so on. The target vector may be any of replacement type and insertion type, and the selection method may be positive selection, promoter selection, negative selection, polyA selection and so on.

As a method for selecting an intended homologous recombinant from the selected cell lines, Southern hybridization method, PCR method and so on for genomic DNA can be mentioned.

The "aggregate" in the present invention refers to a mass of the cells dispersed in the medium but gathered to form same. The "aggregate" in the present invention includes an aggregate formed by the cells dispersed at the start of the floating culture and an aggregate already formed at the start of the floating culture.

When cells are gathered to form cell aggregates and the aggregates are subjected to floating culture, to "form aggregate" means to "rapidly aggregate a given number of dispersed cells" to form qualitatively homogeneous cell aggregates.

In the present invention, it is preferable to rapidly gather pluripotent stem cells to allow formation of an aggregate of pluripotent stem cells. By forming an aggregate of pluripotent stem cells in this manner, an epithelium-like structure can be formed with good reproducibility in the cells induced to differentiate from the formed aggregate.

Examples of the experimental operation to form an aggregate include a method involving keeping cells in a small space using a plate with small wells (96 well plate), micropore and so on, a method involving aggregating cells by centrifugation for a short time using a small centrifugation tube.

Whether aggregates of pluripotent stem cells have been formed and whether an epithelial-like structure has been formed in the cells forming the aggregate can be determined based on the size and cell number of aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

In the present invention, the "tissue" refers to a structure of a cell population, which has a conformation wherein more than one type of cell different in the shape and property are sterically configured in a given pattern.

In the present invention, the "retinal tissue" means a retinal tissue wherein at least two or more types of cells such as photoreceptors, horizontal cells, bipolar cells, amacrin cells, retinal ganglion cells, their progenitor cells or retinal progenitor cells thereof, which constitute respective retinal layers in living retina, are sterically arranged in layers. With regard to each cell, which cell constitutes which retinal layer can be confirmed by a known method, for example, the presence or absence or the level of the expression of a cell marker, and so on.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal layer-specific neural cell" in the present invention means a neural cell constituting a retinal layer and specific to the retinal layer. Examples of the retinal layer-specific neural cell include bipolar cell, ganglion cell, amacrine cell, horizontal cell, photoreceptor, pigment epithelium cell, rod cell and cone cell.

The "retinal pigment epithelial cell" in the present invention means epithelial cells present on the outside of the neuroretinal tissue in biological retina. Whether the cell is a retinal pigment epithelial cell can be confirmed by those of ordinary skill in the art based on, for example, expression of cell markers (RPE65 (pigment epithelium cell), Mitf (pigment epithelium cell) and the like), presence of melanin granule, characteristic cell form of polygon and so on.

The "retinal progenitor cell" in the present invention refers to a progenitor cell that can be differentiated into any mature retinal cell of a photoreceptor, a horizontal cell, a bipolar cell, an amacrine cell, a retinal ganglion cell and a retinal pigment epithelial cell.

The photoreceptor progenitor cell, horizontal progenitor cell, bipolar progenitor cell, amacrine progenitor cell, retinal ganglion progenitor cell and retinal pigment epithelial progenitor cell are progenitor cells determined to differentiate into a photoreceptor, a horizontal cell, a bipolar cell, an amacrine cell, a retinal ganglion cell, and a retinal pigment epithelial cell, respectively.

Examples of the retinal cell marker include Rax and PAX6 expressed in retinal progenitor cells, Nkx2.1 expressed in progenitor cells of hypothalamus neuron but not expressed in retinal progenitor cells, Sox1 expressed in hypothalamus neuroepithelium and not expressed in retina, Crx expressed in progenitor cells of photoreceptor, and so on. Examples of the retinal layer-specific neural cell marker include Chx10 and L7 expressed in bipolar cells, Tuj1 and Brn3 expressed in ganglion cells, Calretinin expressed in amacrine cells, Calbindin expressed in horizontal cells, Rhodopsin and Recoverin expressed in photoreceptors, RPE65 and Mitf expressed in pigment epithelium cells, Nrl expressed in rod cells, Rxr-gamma expressed in cone cells, and so on.

The production method 1 of the present invention is a method for producing retinal pigment epithelial cell, which includes the following steps (1), (2) and (3):
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and
(3) a third step of subjecting the aggregate obtained in step (2) to floating culture in a serum-free medium or serum-containing medium each being free of a substance acting on the Sonic hedgehog signal transduction pathway and a substance acting on the BMP signal transduction pathway and containing a substance acting on the Wnt signal pathway, thereby obtaining an aggregate containing retinal pigment epithelial cell.

Step (1) for subjecting pluripotent stem cells to floating culture in a serum-free medium to form an aggregate of pluripotent stem cells is explained.

The serum-free medium used in step (1) is not particularly limited as long as it is as mentioned above. For example, a serum-free medium not supplemented with any of a substance acting on the BMP signal transduction pathway and a substance inhibiting the Wnt signal pathway can be used. To avoid complicated formulation process, a serum-free medium supplemented with an appropriate amount of a serum replacement such as commercially available KSR (e.g., a medium obtained by adding 10% KSR, 450 μM 1-monothioglycerol and 1× Chemically Defined Lipid Concentrate to a 1:1 mixture of IMDM and F-12) is preferably used. The amount of KSR to be added to a serum-free medium is generally about 1% to about 20%, preferably about 2% to about 20%, in the case of, for example, human ES cells.

The culture conditions such as culture temperature, $CO_2$ concentration in step (1) can be appropriately determined. The culture temperature is, for example, about 30° C. to about 40° C., preferably about 37° C. The $CO_2$ concentration is, for example, about 1% to about 10%, preferably about 5%.

The concentration of the pluripotent stem cells in step (1) can be determined as appropriate to form aggregates of pluripotent stem cells more uniformly and efficiently. For example, when human ES cells are subjected to floating culture using a 96 well microwell plate, a liquid prepared to about $1\times10^3$ to about $5\times10^5$ cells, preferably about $3\times10^3$ to about $5\times10^4$ cells, more preferably about $5\times10^3$ to about $3\times10^4$ cells, most preferably about $1.2\times10^4$ cells, per well is added to a well, and the plate is left standing to form aggregates.

The time of floating culture necessary forming aggregates can be determined as appropriate according to the pluripotent stem cell to be used, to allow for uniform aggregation of the cells. To form uniform aggregates, it is desirably as short as possible. For example, in the case of human ES cells, aggregates are formed preferably within about for 24 hr, more preferably within about for 12 hr. The time for aggregate formation can be appropriately adjusted by controlling the tools for aggregating the cells, centrifugation conditions and so on.

Whether aggregates of pluripotent stem cells have been formed can be determined based on the size and cell number of aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

Step (2) including subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells is explained.

As the medium to be used in step (2), for example, a serum-free medium or a serum-containing medium not supplemented with a substance acting on the Sonic hedgehog signal transduction pathway and supplemented with a substance acting on the BMP signal transduction pathway is used, and addition of a basement membrane preparation is not necessary.

The serum-free medium or serum-containing medium to be used as such medium is not particularly limited as long as it is as mentioned above. To avoid complicated formulation process, a serum-free medium supplemented with an appropriate amount of a serum replacement such as commercially available KSR (e.g., a medium obtained by adding 10% KSR, 450 µM 1-monothioglycerol and 1× Chemically Defined Lipid Concentrate to a 1:1 mixture of IMDM and F-12) is preferably used. The amount of KSR to be added to a serum-free medium is generally about 1% to about 20%, preferably about 2% to about 20%, in the case of, for example, human ES cells.

As the serum-free medium to be used in step (2), the serum-free medium used in step (1) may be used as it is as long as it does not contain a substance acting on the Sonic hedgehog signal transduction pathway, or may be replaced with a fresh serum-free medium. When the serum-free medium used in step (1) is directly used for step (2), a substance acting on the BMP signal transduction pathway only needs to be added to the medium.

A substance acting on the Sonic hedgehog (hereinafter sometimes referred to as Shh) signal transduction pathway is a substance that can enhance signal transduction mediated by Shh. Examples of the substance acting on the Shh signal transduction pathway include proteins belonging to the Hedgehog family (e.g., Shh), Shh receptor, Shh receptor agonist, Purmorphamine, SAG and so on.

A medium "free of a substance acting on the Sonic hedgehog signal transduction pathway" also includes a medium substantially free of a substance acting on the Sonic hedgehog signal transduction pathway, such as a medium free of a substance acting on the Sonic hedgehog signal transduction pathway, at a concentration exerting an adverse influence on the selective differentiation into retinal progenitor cell and retinal tissue.

A medium "not supplemented with a substance acting on the Sonic hedgehog signal transduction pathway" also includes a medium substantially not supplemented with a substance acting on the Sonic hedgehog signal transduction pathway, such as a medium not supplemented with a substance acting on the Sonic hedgehog signal transduction pathway, at a concentration exerting an adverse influence on the selective differentiation into retinal progenitor cell and retinal tissue.

A substance acting on the BMP signal transduction pathway is a substance that can enhance signal transduction pathway mediated by BMP. Examples of the substance acting on the BMP signal transduction pathway include BMP proteins such as BMP2, BMP4 or BMP7, GDF proteins such as GDF7, anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd.

The concentration of a substance acting on the BMP signal transduction pathway only needs to be a concentration capable of inducing differentiation of cells forming pluripotent stem cell aggregates into retinal cells. In the case of BMP4, for example, it is added to a medium at a concentration of about 0.01 nM to about 1 µM, preferably about 0.1 nM to about 100 nM, more preferably about 1.5 nM.

A substance acting on the BMP signal transduction pathway only needs to be added after about 24 hours from the start of the floating culture in step (1), and may be added to the medium within several days from the start of the floating culture (e.g., within 15 days). Preferably, a substance acting on the BMP signal transduction pathway is added to the medium between day 1 and day 15, more preferably between day 1 and day 9, most preferably at day 3, from the start of the floating culture.

After a substance acting on the BMP signal transduction pathway is added to the medium and differentiation induction of cells forming pluripotent stem cell aggregates into retinal cells is started, the substance acting on the BMP signal transduction pathway does not need to be added to the medium, and the medium can be exchanged with a serum-free medium or serum-containing medium each being free of a substance acting on the BMP signal transduction pathway, whereby the cost of the medium can be suppressed. A cell in which differentiation induction into a retinal cell has been started can be confirmed, for example, by detecting the expression of Rax gene in the cell. It is also possible to confirm the time when the differentiation induction into retinal cell was started by subjecting the aggregates formed in step (1) using a pluripotent stem cell, in which a fluorescence reporter protein gene such as GFP has been knocked-in in the Rax gene locus, to floating culture in the presence of a substance acting on the BMP signal transduction pathway at a concentration necessary for differentiation induction into retinal cells, and detecting the fluorescence emitted from the expressed fluorescence reporter protein. One of the embodiments of step (2) is a step including subjecting the aggregates formed in step (1) to floating culture in a serum-free medium or serum-containing medium each containing a substance acting on the BMP signal transduction pathway at a concentration necessary for differentiation induction into retinal cells and being free of a substance acting on the Sonic hedgehog signal transduction pathway until a cell expressing the Rax gene appears to obtain an aggregate containing a retinal progenitor cell.

The culture conditions such as culture temperature, $CO_2$ concentration in step (2) can be appropriately determined. The culture temperature is, for example, about 30° C. to about 40° C., preferably about 37° C. The $CO_2$ concentration is, for example, about 1% to about 10%, preferably about 5%.

That an aggregate containing a retinal progenitor cell has been obtained can be confirmed by, for example, detecting the presence of a cell expressing a retinal progenitor cell marker Rax or PAX6 in the aggregate.

The step (3) including subjecting the aggregate obtained in step (2) to floating culture in a serum-free medium or serum-containing medium each being free of a substance acting on the Sonic hedgehog signal transduction pathway and a substance acting on the BMP signal transduction pathway and containing a substance acting on the Wnt signal pathway, thereby obtaining an aggregate containing retinal pigment epithelial cell is explained.

The medium used in step (3) is, for example, a serum-free medium or serum-containing medium not supplemented with any of a substance acting on the Sonic hedgehog signal transduction pathway and a substance acting on the BMP signal transduction pathway, and supplemented with a substance acting on the Wnt signal pathway.

The medium "free of a substance acting on the Sonic hedgehog signal transduction pathway and a substance acting on the BMP signal transduction pathway" also includes a medium substantially free of a substance acting on the Sonic hedgehog signal transduction pathway and a substance acting on the BMP signal transduction pathway, for example, a medium not containing a substance acting on the Sonic hedgehog signal transduction pathway and a substance acting on the BMP signal transduction pathway, at a concentration exerting an adverse influence on the selective differentiation into retinal tissues.

The medium "not supplemented with any of a substance acting on the Sonic hedgehog signal transduction pathway and a substance acting on the BMP signal transduction pathway" also includes a medium substantially not supplemented with a substance acting on the Sonic hedgehog signal transduction pathway and a substance acting on the BMP signal transduction pathway, for example, a medium not supplemented with a substance acting on the Sonic hedgehog signal transduction pathway and a substance acting on the BMP signal transduction pathway, at a concentration exerting an adverse influence on the selective differentiation into retinal tissues.

Examples of the serum-free medium or serum-containing medium to be used as such medium include the media mentioned above. Preferred is a serum-free medium which is a basal medium such as DMEM-F12 medium supplemented with a mixture of neurotrophic factors such as N2 supplement (Invitrogen), B27 supplement (Invitrogen) and not supplemented with KSR.

The substance acting on the Wnt signal pathway is a substance that can enhance signal transduction mediated by Wnt. Examples of the substance acting on the Wnt signal pathway include protein belonging to Wnt family (e.g., Wnt1, Wnt3a, Wnt7a), Wnt receptor agonist, GSK3β inhibitor (e.g., 6-Bromoindirubin-3'-oxime (BIO), CHIR99021, Kenpaullone) and so on.

The concentration of the substance acting on the Wnt signal pathway may be any as long as differentiation of the cells forming pluripotent stem cell aggregates into retinal cells can be induced. For example, in the case of CHIR99021, it is added at a concentration of about 0.1 µM to about 100 µM, preferably about 1 µM to about 30 µM, more preferably about 3 µM.

A substance acting on the Wnt signal pathway is added, for example, not earlier than day 12 from the start of the floating culture in step (1), preferably on day 18, when human ES cells are used.

In step (3), it is more preferable to culture aggregates in a serum-free medium or serum-containing medium each being free of a substance acting on the Sonic hedgehog signal transduction pathway and a substance acting on the BMP signal transduction pathway, and containing a substance acting on the Wnt signal pathway and a substance inhibiting the FGF signal pathway.

A substance inhibiting the FGF signal pathway is a substance capable of inhibiting a signal mediated by FGF. Examples of the substance inhibiting the FGF signal pathway include FGF receptor, FGF receptor inhibitor (e.g., SU-5402, AZD4547, BGJ398), MAP kinase cascade inhibitory substance (e.g., MEK inhibitor, MAPK inhibitor, ERK inhibitor), PI3 kinase inhibitor, Akt inhibitor and the like.

The concentration of a substance inhibiting the FGF signal pathway to be used in step (3) may be any as long as differentiation of the cells forming pluripotent stem cell aggregates into retinal cells can be induced. For example, in the case of SU-5402, it is added at a concentration of about 0.1 µM to about 100 µM, preferably about 1 µM to about 30 µM, more preferably about 10 µM.

Since the thus-produced retinal pigment epithelial cells are present on the surface of an aggregate, they can be confirmed by microscopic observation and the like. It is also possible to obtain a highly pure retinal pigment epithelial cell by subjecting the aggregate containing retinal pigment epithelial cells to a dispersion treatment (e.g., trypsin/EDTA treatment), and selecting the resulting cells by using FACS. It is also possible to physically cut out retinal pigment epithelial cells from the aggregate by using tweezers and the like, and culture the cells. The retinal pigment epithelial cells thus dispersed or cut out can be cultured under adhesion conditions. It is also possible to disrupt aggregates containing retinal pigment epithelial cells by a pipetting operation using a micropipette, etc., and further culture the resulting cells under adhesion conditions. In the case of adhesion culture, a cell adhesive culture vessel, for example, a culture vessel after a coating treatment with an extracellular matrix etc. (e.g., poly-D-lysine, laminin, fibronectin), is preferably used. The culture conditions of the adhesion culture such as culture temperature, $CO_2$ concentration, and $O_2$ concentration can be determined as appropriate. In this case, the cells may be cultured in the presence of a serum, a known growth factor, and additives and chemical substances that promote growth. Examples of the known growth factor include EGF, FGF and the like. Examples of the additives that promote growth include N2 supplement (Invitrogen), B27 supplement (Invitrogen) and the like.

The production method 2 of the present invention is a method for producing a retinal pigment epithelial cell sheet, comprising the following steps (1), (2), (3) and (4):

(1) a first step of subjecting pluripotent stem cells to floating culture in a serum-free medium to form an aggregate of pluripotent stem cells, (2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, (3) a third step of subjecting the aggregate obtained in step (2) to floating culture in a serum-free medium or serum-containing medium each being free of a substance acting on the Sonic hedgehog signal transduction pathway and a substance acting on the BMP signal transduction pathway and containing a substance acting on the Wnt signal pathway, thereby obtaining an aggregate containing retina progenitor cell, and (4) a fourth step of dispersing the aggregate obtained in step (3) and subjecting the resulting cells to adhesion culture.

The step (1), step (2) and step (3) of the production method 2 of the present invention can be performed similarly to step (1), step (2) and step (3) of the production method 1 of the present invention.

Step (4) for dispersing the aggregate obtained in step (3) and subjecting the resulting cells to adhesion culture is explained.

Step (4) is performed within 60 days, preferably within 30 days, more preferably 3 days, after the start of step (3).

The cells derived from the aggregates dispersed in step (4) are seeded in an adhesion culture container to a concentration capable of efficiently forming a uniform sheet of retinal pigment epithelial cells. For example, when cells derived from the aggregates are subjected to adhesion culture using a 65 mm Boyden chamber, a solution prepared to contain about $1 \times 10^3$ to about $1 \times 10^7$ cells, preferably about $3 \times 10^3$ to about $5 \times 10^6$ cells, more preferably about $5 \times 10^3$ to about $1 \times 10^6$ cells, further preferably about $2 \times 10^5$ cells, per well is added to wells, and the plate is stood to allow the cells derived from the aggregates to adhere and cultivate.

Examples of the serum-free medium or serum-containing medium to be used for the adhesion culture in step (4) include the aforementioned media. To avoid complicated formulation process, for example, a serum-free medium supplemented with an appropriate amount of a serum replacement such as commercially available KSR (e.g., medium wherein 1:1 mixture of DMEM/F-12 and Neurobasal is added with ½×N2 supplement, ½×B27 supplement and 100 µM 2-mercaptoethanol) is preferably used. The concentration of KSR to be added to a serum-free medium is generally about 1% to about 20%, preferably about 2% to about 20%, in the case of, for example, cells derived from human ES cells.

In step (4), the cells are preferably cultured in a serum-free medium or serum-containing medium containing a ROCK inhibitory substance.

The ROCK inhibitory substance is a substance capable of inhibiting a signal mediated via a Rho kinase. Examples of the ROCK inhibitory substance include Y-27632 and Fasudil.

The concentration of a ROCK inhibitory substance to be used in step (4) may be any as long as a uniform sheet of retinal pigment epithelial cells can be efficiently formed. For example, in the case of Y-27632, it is added at a concentration of about 0.01 µM to about 100 µM, preferably about 1 µM to about 30 µM, more preferably about 20 µM.

In step (4), it is more preferable to culture the cells in a serum-free medium or serum-containing medium further containing one or more substances selected from the group consisting of a substance acting on the Wnt signal pathway, a substance inhibiting the FGF signal pathway, a substance acting on the Activin signal pathway and a substance acting on the BMP signal transduction pathway.

Examples of the substance acting on the Wnt signal pathway include protein belonging to Wnt family (e.g., Wnt1, Wnt3a, Wnt7a), Wnt receptor agonist, GSK3β inhibitor (e.g., 6-Bromoindirubin-3'-oxime (BIO), CHIR99021, Kenpaullone) and the like.

The concentration of a substance acting on the Wnt signal pathway to be used in step (4) may be any as long as a uniform sheet of retinal pigment epithelial cells can be efficiently formed. For example, in the case of CHIR99021, it is added at a concentration of about 0.1 µM to about 100 µM, preferably about 1 µM to about 30 µM, more preferably about 3 µM.

A substance acting on the Wnt signal pathway is added, for example, within 18 days, preferably on day 6, from the start of step (4).

Examples of the substance inhibiting the FGF signal pathway include FGF receptor, FGF receptor inhibitor (e.g., SU-5402, AZD4547, BGJ398), MAP kinase cascade inhibitory substance (e.g., MEK inhibitor, MAPK inhibitor, ERK inhibitor), PI3 kinase inhibitor, and Akt inhibitor.

The concentration of a substance inhibiting the FGF signal pathway to be used in step (4) may be any as long as a uniform sheet of retinal pigment epithelial cells can be efficiently formed. For example, in the case of SU-5402, it is added at a concentration of about 0.1 µM to about 100 µM, preferably about 1 µM to about 30 µM, more preferably about 10 µM.

A substance inhibiting the FGF signal pathway is added, for example, within 18 days, preferably on day 6, from the start of step (4).

A substance acting on the Activin signal pathway is a substance capable of enhancing a signal mediated by Activin. Examples of the substance acting on the Activin signal pathway include proteins belonging to the Activin family (e.g., Activin A, Activin B, Activin C, Activin AB etc.), Activin receptor and Activin receptor agonist.

The concentration of a substance acting on the Activin signal pathway to be used in step (4) may be any as long as a uniform sheet of retinal pigment epithelial cells can be efficiently formed. For example, in the case of Recombinant Human/Mouse/Rat Activin A (R&D Systems, Inc. #338-AC), it is added at a concentration of about 1 ng/ml to about 10 µg/ml, preferably about 10 ng/ml to about 1 µg/ml, more preferably about 100 ng/ml.

A substance acting on the Activin signal pathway is added, for example, within 18 days, preferably on 6 day, from the start of step (4).

Examples of the substance acting on the BMP signal transduction pathway include BMP proteins such as BMP2, BMP4 or BMP7 and, GDF proteins such as GDF7, and so on, anti-BMP receptor antibody, BMP partial peptide and the like.

The concentration of a substance acting on the BMP signal transduction pathway to be used in step (4) may be any as long as a uniform sheet of retinal pigment epithelial cells can be efficiently ft/med. For example, in the case of BMP4, it is added at a concentration of about 0.01 nM to about 1 µM, preferably about 0.1 nM to about 100 nM, more preferably about 1.5 nM.

A substance acting on the BMP signal transduction pathway is added, for example, within 18 days, preferably on day 6, from the start of step (4).

In step (4), for example, cells are cultured in a serum-free medium or serum-containing medium further containing one kind of substance selected from the group consisting of a substance acting on the Wnt signal pathway, a substance inhibiting the FGF signal pathway, a substance acting on the Activin signal pathway and a substance acting on the BMP signal transduction pathway, or a serum-free medium or serum-containing medium further containing a substance acting on the Wnt signal pathway and a substance inhibiting the FGF signal pathway.

In step (4), the adhesion culture is preferably performed on culture vessel material which is surface-treated with a culture substrate.

As a culture substrate used for treating culture vessel material in step (4), a cell culture substrate permitting adhesion culture of cells derived from aggregate, and formation of a retinal pigment epithelial cell sheet can be mentioned. To avoid complicated preparation and prevent contamination of component(s) derived from a heterologous species, use of a synthetic culture substrate, a basement membrane component derived from human, a recombinant human basement membrane protein and so on is preferable. Specific examples of such culture substrate include synthetic culture substrates such as SYNTHEMAX™ substrate (Corning incorporated) and so on, basement membrane components derived from human such as CELLSTART™ substrate (Invitrogen), human extracellular substrate (BD) and so on, recombinant human laminin such as human recombinant laminin111 (Biolamina), human recombinant laminin511 (Biolamina), human recombinant laminin521 (Biolamina), human recombinant laminin411 (Biolamina), human recombinant laminin421 (Biolamina), human recombinant laminin332 (Biolamina) and human recombinant laminin211 (Biolamina) and so on. As used herein, laminin111 is a laminin consisting of α1 chain, β1 chain and γ1 chain, laminin511 is a laminin consisting of α5 chain, β1 chain and γ1 chain, laminin521 is a laminin consisting of α5 chain, β2 chain and γ1 chain, laminin411 is a laminin consisting of α4 chain, β1 chain and γ1 chain, laminin421 is a laminin consisting of α4 chain, β2 chain and γ1 chain, laminin332 is a laminin consisting of α3 chain, β3 chain and γ2 chain, and laminin211 is a laminin consisting of α2 chain, β1 chain and γ1 chain. Furthermore, a part called E8 fragment, which is constituted of the C-terminal region of each of the α chain, β chain and γ chain of laminin, is also known to show a binding activity to integrin expressed by cells (J. Biol. Chem., 284, 7820-7831 (2009)). Therefore, it is expected to be similarly usable as the above-mentioned laminin.

A retinal pigment epithelial cell or retinal pigment epithelial cell sheet produced by the production method 1 or 2 of the present invention has characteristics extremely similar to those of retinal pigment epithelial cells in the body. Therefore, it can also be used for screening for a therapeutic drug for a disease due to a disorder of retinal cells, or a transplantation material for cell treatment, a material for the study of diseases or a drug discovery material for a therapeutic drug for a cell damage due to other etiology. In addition, they can be utilized for the study of toxicity such as phototoxicity, toxicity test and so on in the toxicity and drug efficacy evaluation of chemical substances and so on.

Examples of the disease due to a disorder of retinal cells include organic mercury poisoning, chloroquine retinopathy, retinitis pigmentosa, age-related macular degeneration, glaucoma, diabetic retinopathy, neonatal retinopathy, and so on.

A retinal pigment epithelial cell or retinal pigment epithelial cell sheet produced by the production method 1 or 2 of the present invention can be used as a retinal pigment epithelial cell for transplantation, which is used for supplementing a damaged cell or disordered tissue itself in a cell damage state (e.g., used for transplantation operation) and so on.

EXAMPLES

The present invention is explained in more detail in the following by referring to Examples, which are not to be construed as limitative.

Example 1: Production of Retinal Pigment Epithelial Cell Using Human ES Cells

Human ES cells (KhES-1-derived) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells using TrypLE Express (Invitrogen), and the singly dispersed ES cells were suspended in 100 µl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates, and subjected to culture at 37° C., 5% $CO_2$. As the serum-free medium therefor, a serum-free medium obtained by adding 10% KSR, 450 µM 1-monothioglycerol, 1× Chemically defined lipid concentrate, 20 µM Y27632 to a 1:1 mixture of F-12 medium and IMDM medium was used. At day 3 from the start of the floating culture, BMP4 was added at a final concentration 1.5 nM, and the floating culture was continued. A half amount of the culture medium in the well was exchanged every 3 days with the above-mentioned medium not supplemented with a substance acting on the BMP signal transduction pathway. At day 18 from the start of the floating culture, aggregates were transferred to a serum-free medium, which was DMEM/F-12 medium containing 3 µM CHIR99021 and added with 1× N2 supplement, and cultured until day 21 from the start of the floating culture, and microscope observation was performed.

At day 18 from the start of the floating culture, formation of neuroepithelium was confirmed (FIG. 1A). At day 21 from the start of the floating culture, differentiation of cells into retinal pigment epithelial cells having thin epithelium was confirmed (FIG. 1B).

Example 2: Production of Retinal Pigment Epithelial Cell Using Human ES Cells

Human ES cells (KhES-1-derived) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells using TrypLE Express (Invitrogen), and the singly dispersed ES cells were suspended in 100 µl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates, and subjected to culture at 37° C., 5% $CO_2$. As the serum-free medium therefor, a serum-free medium obtained by adding 10% KSR, 450 µM 1-monothioglycerol, 1× Chemically defined lipid concentrate, 20 µM Y27632 to a 1:1 mixture of F-12 medium and IMDM medium was used. At day 3 from the start of the floating culture, BMP4 was added at a final concentration 1.5 nM, and the floating culture was continued. A half amount of the culture medium in the well was exchanged every 3 days with the above-mentioned medium not supplemented with a substance acting on the BMP signal transduction pathway. At day 18 from the start of the floating culture, aggregates were transferred to a serum-free medium, which was DMEM/F-12 medium containing 3 µM CHIR99021 and added with 1× N2 supplement, and floating culture was continued until day 21 from the start of the floating culture. As a control, aggregates were similarly cultured even in the absence of CHIR99021. A part of the aggregates subjected to floating culture in the aforementioned medium containing CHIR99021 underwent floating culture under the same medium conditions until day 27 from the start of the floating culture, and the other part underwent floating culture in a serum-free medium, which was DMEM/F-12 medium containing 3 μM CHIR99021 (a substance acting on the Wnt signal pathway) and 10 μM SU-5402 (a substance inhibiting the FGF signal pathway) and added with 1× N2 supplement, from day 21 to day 27 from the start of the floating culture at 37° C., 5% $CO_2$.

Figure 2:
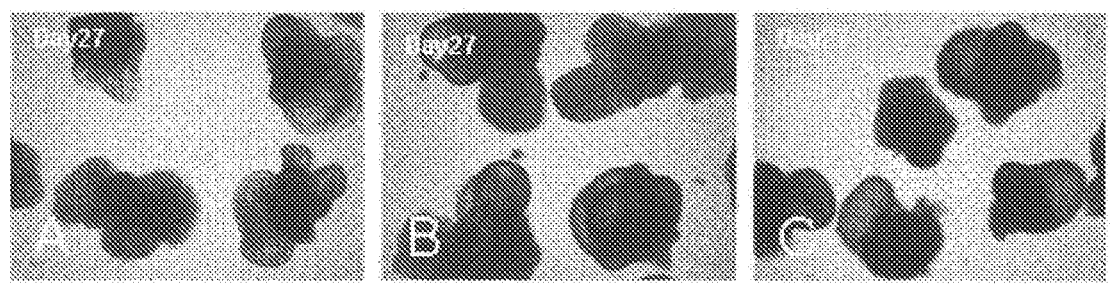
FIG. 2 shows (A) a bright field image at day 27 of floating culture in a medium free of BMP4 and containing CHIR99021 from days 18 to 21 of the floating culture and thereafter in a medium free of BMP4 and CHIR99021, (B) a bright field image at day 27 of floating culture in a medium free of BMP4 and containing CHIR99021 from days 18 to 27 of the floating culture, and (C) a bright field image at day 27 of floating culture in a medium free of BMP4 and containing CHIR99021 from days 18 to 21 of the floating culture, in a medium free of BMP4 and containing CHIR99021 and SU-5402 from days 21 to 27 of the floating culture, of human embryonic stem cells-derived aggregates floating cultured in a medium containing BMP4 for days 3-18 from the start of the floating culture.

The aggregates cultured in the absence of a substance acting on the Wnt signal pathway from day 21 of culture, retinal pigment epithelium having thin epithelium returned to neuroepithelium having thick epithelium (FIG. 2A), whereas in the aggregates continued to be cultured in the presence of a substance acting on the Wnt signal pathway, dark retinal pigment epithelial cells appeared on the surface of almost all aggregates (FIG. 2B). The aggregates cultured in the presence of a substance acting on the Wnt signal pathway and a substance inhibiting the FGF signal pathway showed an increase in the differentiation induction efficiency, and aggregates having retinal pigment epithelial cells on almost all the surface of the aggregates were formed (FIG. 2C).

Example 3: Production of Retinal Pigment
Epithelial Cell Using Human ES Cells

Human ES cells (KhES-1-derived) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells using TrypLE Express (Invitrogen), and the singly dispersed ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates, and subjected to culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium was used. At day 3 from the start of the floating culture, BMP4 was added at a final concentration 1.5 nM, and floating culture was continued. A half amount of the culture medium in the well was exchanged every 3 days with the above-mentioned medium not supplemented with a substance acting on the BMP signal transduction pathway. At day 18 from the start of the floating culture, the aggregates were transferred to a serum-free medium, which was DMEM/F-12 medium containing 3 μM CHIR99021 and added with 1× N2 supplement, and floating culture was continued until day 21 from the start of the floating culture. At day 21 from the start of the floating culture, the aggregates were disrupted by injecting and ejecting solution by micropipette, and the resulting cells were subjected to adhesion culture in a serum-free medium, which was DMEM/F-12 medium containing 3 μM CHIR99021 (a substance acting on the Wnt signal pathway) and added with 1× N2 supplement, at 37° C., 5% $CO_2$.

Figure 3:
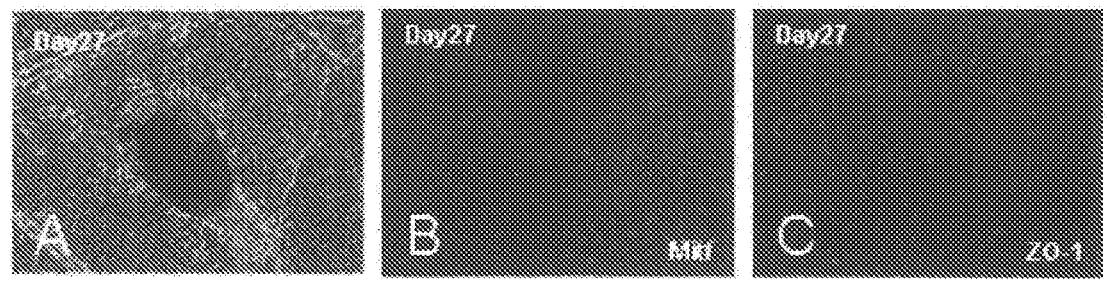
FIG. 3 shows (A) a bright field image, (B) a fluorescence immunostaining image of retinal pigment epithelial marker Mitf, and (C) a fluorescence immunostaining image of tight junction marker ZO-1, each at day 27 from the start of the floating culture, of adhesion cultured cells in a medium containing CHIR99021 wherein the cells were obtained by floating culture of human embryonic stem cells-derived aggregates in a medium containing BMP4 from days 3 to 18 of the floating culture, in a medium free of BMP4 and containing CHIR99021 from days 18 to 21 of the floating culture, and disruption of the aggregates on day 21 of the culture.

By day 27 from the start of the floating culture, retinal pigment epithelial cells having a characteristic polygonal cell form were observed (FIG. 3A). The expression of protein was confirmed by a cell staining method. As a result, the cells were positive to the transcription factor Mitf, which is a retinal pigment epithelial cell marker (FIG. 3B) and positive to ZO-1, which is a tight junction marker (FIG. 3C), from which it was confirmed that the obtained cells were retinal pigment epithelial cells.

Example 4: Production of Retinal Pigment
Epithelial Cell Sheet Using Human ES Cells Human ES cells (KhES-1-derived) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells using TrypLE Express (Invitrogen), and the singly dispersed ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates, and subjected to culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium was used. At day 3 from the start of the floating culture, BMP4 was added at a final concentration 1.5 nM, and floating culture was continued. A half amount of the culture medium in the well was exchanged every 3 days with the above-mentioned medium not supplemented with a substance acting on the BMP signal transduction pathway. At day 18 from the start of the floating culture, the aggregates were transferred to a serum-free medium, which was DMEM/F-12 medium containing 3 μM CHIR99021 and added with 1× N2 supplement, and cultured until day 21 from the start of the floating culture. At day 21 from the start of the floating culture, the aggregates were dispersed in cell dispersion solution Accutase (ICT), and debris was removed using a 40 μm cell strainer. The resulting cells were suspended in a serum-free medium (200 μl), which was a 1:1 mixture of DMEM/F-12 medium and Neurobasal medium added with 10% KSR, ½ N2 supplement, ½ B27 supplement, 20 μM Y27632, and seeded in a 65 mm Boyden chamber (Transwell, Corning Incorporated) after a coating treatment with SYNTHEMAX™ substrate at $2 \times 10^5$ cells per well, a medium (1 ml) having the same composition was also added to a lower well, and adhesion culture was performed at 37° C., 5% $CO_2$. The medium was exchanged every 3 days, and the level of epithelial formation was observed under a microscope at day 40 from the start of the floating culture.

Figure 4:
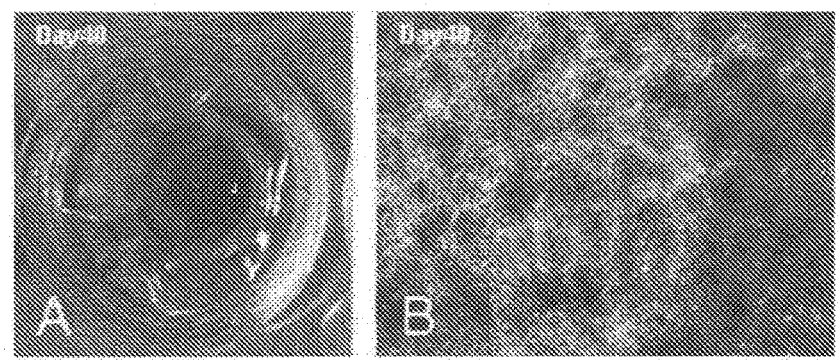
FIG. 4 shows (A) an image of a retinal pigment epithelial cell sheet and (B) an enlarged image of the light field, each on day 40 from the start of the floating culture, of adhesion cultured cells in a medium containing Y27632 wherein the cells were obtained by floating culture of human embryonic stem cells-derived aggregates in a medium containing BMP4 from days 3 to 18 of the floating culture, in a medium free of BMP4 and containing CHIR99021 from days 18 to 21 of the floating culture, dispersion on day 21 of the floating culture, and seeding of the resulting cells in a Boyden chamber surface-treated with SYNTHEMAX™ substrate.

By day 40 from the start of the floating culture, a uniform retinal pigment epithelial cell sheet having a characteristic polygonal cell form (FIG. 4B) with pigment accumulation was formed (FIG. 4A).

Example 5: Production of Retinal Pigment
Epithelial Cell Sheet Using Human ES Cells Human ES cells (KhES-1-derived) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells using TrypLE Express (Invitrogen), and the above-mentioned cultured ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates and subjected to culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium was used. At day 3 from the start of the floating culture, BMP4 was added al a concentration 1.5 nM, and floating culture was continued. A half amount of the culture medium in the well was exchanged every 3 days with the above-mentioned medium not supplemented with a substance acting on the BMP signal transduction pathway. At day 18 from the start of the floating culture, the aggregates were transferred to a serum-free medium, which was DMEM/F-12 medium containing 3 μM CHIR99021 and added with 1× N2 supplement, and cultured until day 21 from the start of the floating culture. At day 21 from the start of the floating culture, the aggregates were dispersed in cell dispersion solution Accutase (ICT), and debris was removed using a 40 μm cell strainer. The resulting cells were suspended in a serum-free medium (200 μl), which was a 1:1 mixture of DMEM/F-12 medium and Neurobasal medium added with 10% KSR, ½ N2 supplement, ½ B27 supplement, 20 μM Y27632, and seeded in a 65 mm Boyden chamber (Transwell, Corning Incorporated) after a coating treatment with SYNTHEMAX™ substrate at $2 \times 10^5$ cells per well, a medium (1 ml) having the same composition was also added to a lower well, and adhesion culture was performed at 37° C., 5% $CO_2$. At day 24 from the start of the floating culture, namely, at day 3 from the start of the adhesion culture, 3 μM CHIR99021 was added, 10 μM SU-5402 was added, 3 μM CHIR99021 and 10 μM SU-5402 were simultaneously added, 1 nM recombinant human BMP4 protein was added, or 50 ng/ml recombinant human activin was added, and the adhesion culture was continued. Similar culture was performed under conditions free of the addition of the aforementioned substances. The medium was exchanged every 3 days, and the level of epithelial formation was observed under a microscope at day 40 from the start of the floating culture.

Figure 5:
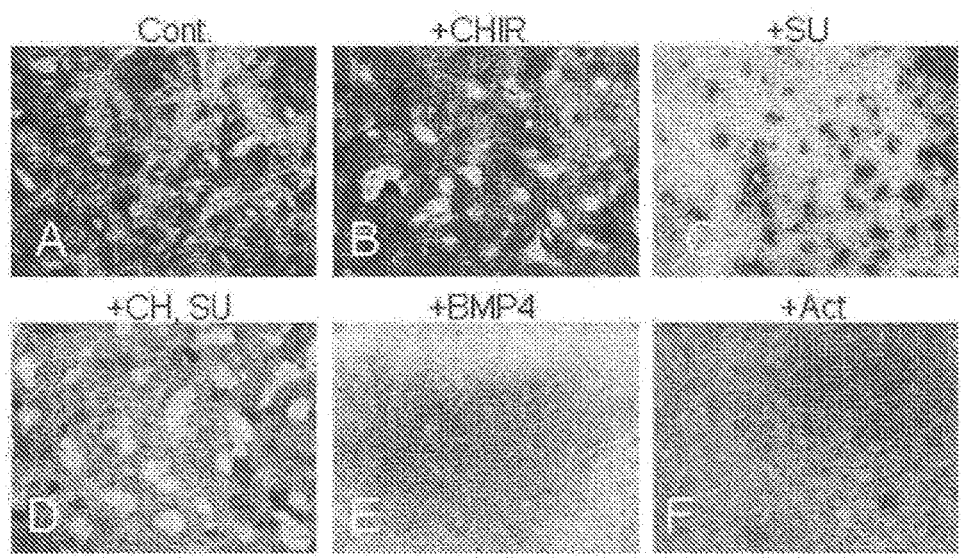
FIG. 5 shows enlarged images of the light field of a retinal pigment epithelial cell sheet on day 40 from the start of the floating culture. Human embryonic stem cells-derived aggregates were underwent floating culture in a medium containing BMP4 from day 3 to day 18 of the floating culture, in a medium free of BMP4 and containing CHIR99021 from day 18 to day 21 of the floating culture, dispersion on day 21 of the culture, seeding of the resulting cells in a Boyden chamber surface-treated with SYNTHEMAX™ substrate and adhesion culture thereof. The adhesion culture was continued until day 40 from the start of the floating culture, (A) without addition of components, or with the addition of (B) 3 µM CHIR99021, (C) 10 µM SU-5402, (D) 3 µM CHIR99021 and 10 µM SU-5402, (E) 1 nM human BMP4 protein, or (F) 50 ng/ml human activin on day 24 from the start of the floating culture, or day 3 from the start of the adhesion culture.

When 3 μM CHIR99021 was added at day 24 from the start of the floating culture (FIG. 5B), the cells differentiated into darker retinal pigment epithelial cells as compared to the control free of the addition (FIG. 5A). By simultaneous addition of 3 μM CHIR99021 and 10 μM SU-5402 (FIG. 5D), pigment epithelium colored darker than by a single addition of 3 μM CHIR99021 (FIG. 5B) was obtained. When 1 nM recombinant human BMP4 protein was added (FIG. 5E), or 50 ng/ml recombinant human activin was added (FIG. 5F), more uniform epithelium was obtained as compared to the control free of the addition (FIG. 5A).

Example 6: Production of Retinal Pigment Epithelial Cell Sheet Using Human ES Cells Growth Factor Reduced MATRIGEL™ extracellular matrix (diluted 30-fold), or SYNTHEMAX™ substrate (Corning Incorporated) (diluted 40-fold) was added by 100 μl each to the wells of a 65 mm Boyden chamber (Transwell, Corning Incorporated). The above-mentioned chamber added with MATRIGEL™ extracellular matrix was incubated at 4° C. for 24 hr, and the above-mentioned chamber added with SYNTHEMAX™ substrate was incubated at room temperature for 2 hr, whereby a coating treatment of the culture vessel materials was performed. A single cell suspension was prepared from the aggregates at day 21 from the start of the floating culture by the method described in Example 4, the suspended cells were seeded in a serum-free medium (200 μl), which was a 1:1 mixture of DMEM/F-12 medium and Neurobasal medium added with 10% KSR, ½ N2 supplement, ½ B27 supplement, 20 μM Y27632 at $2 \times 10^5$ cells per well, a medium (1 ml) having the same composition was also added to a lower well, and adhesion culture was performed at 37° C., 5% $CO_2$. Adhesion and epithelium formation of the cells were observed at day 5 from the seeding to a Boyden chamber.

Figure 6:
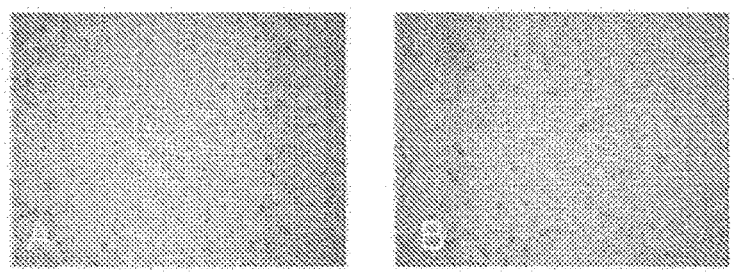
FIG. 6 shows images of a retinal pigment epithelial sheet on day 26 from the start of the floating culture, of adhesion cultured cells which seeded in a Boyden chamber surface-treated with either (A) MATRIGEL™ extracellular matrix or (B) SYNTHEMAX™ substrate wherein the cells were obtained by floating culture of human embryonic stem cells-derived aggregates in a medium containing BMP4 from day 3 to day 18 of the floating culture, in a medium free of BMP4 and containing CHIR99021 from day 18 to day 21 of the floating culture, and dispersion on day 21 of the floating culture.

In a culture vessel material coated with SYNTHEMAX™ substrate (FIG. 6B), cultured cells derived from the aggregates adhered, in the same manner as in a culture vessel material coated with MATRIGEL™ extracellular matrix, which is a basement membrane preparation (FIG. 6A), and a retinal pigment epithelial-like form wherein cells are closely adhered to each other, was observed.

Example 7: Production Example of Retinal Pigment Epithelial Cell Using Induced Pluripotent Stem Cells (iPS Cells)

Human iPS cell line 201B7 (available from RIKEN BioResource center or iPS Academia Japan Inc.) is cultivated according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) is used. The cultured iPS cells are dispersed into single cells using TrypLE Express (Invitrogen), suspended in 100 μl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates and subjected to floating culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium is used. At day 3 from the start of the floating culture, BMP4 is added at a final concentration of 1.5 nM, and the floating culture is continued. A half amount of the culture medium in the well is exchanged every 3 days with the above-mentioned medium not supplemented with any substance acting on the BMP signal transduction pathway. At day 18 from the start of the floating culture, the aggregates are transferred to a serum-free medium, which was DMEM/F-12 medium containing 3 μM CHIR99021 and added with 1× N2 supplement, and cultured until day 21 from the start of the floating culture. At day 21 from the start of the floating culture, the aggregates are disrupted by injecting and ejecting the solution by a micropipette, and the resulting cells are subjected to adhesion culture in a serum-free medium, which is DMEM/F-12 medium containing 3 μM CHIR99021 (a substance acting on the Wnt signal pathway) and added with 1× N2 supplement, at 37° C., 5% $CO_2$. At day 27 from the start of the floating culture, cell form is observed under a microscope and expression of retinal pigment epithelial marker genes (Mitf, ZO-1) is confirmed by a cell staining method.

In this way, retinal pigment epithelial cells are produced from human iPS cells.

Example 8: Production Example of Retinal Pigment Epithelial Cell Sheet Using Induced Pluripotent Stem Cells (iPS Cells)

Human iPS cell line 201B7 (available from RIKEN BioResource center or iPS Academia Japan Inc.) is cultivated according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) is used. The cultured iPS cells are dispersed into single cells using TrypLE Express (Invitrogen), suspended in 100 µl of a serum-free medium at $1.2 \times 10^4$ cells per one well of a non-cell adhesive 96 well culture plate (sumilon spheroid plates, SUMITOMO BAKELITE Co., Ltd.) to allow for rapid formation of aggregates and subjected to floating culture at 37° C., 5% $CO_2$. As the serum-free medium therefor, a serum-free medium obtained by adding 10% KSR, 450 µM 1-monothioglycerol, 1× Chemically defined lipid concentrate, 20 µM Y27632 to a 1:1 mixture of F-12 medium and IMDM medium is used. At day 3 from the start of the floating culture, BMP4 is added at a final concentration of 1.5 nM and floating culture is continued. A half amount of the culture medium in the well is exchanged every 3 days with the above-mentioned medium not supplemented with a substance acting on the BMP signal transduction pathway. At day 18 from the start of the floating culture, the aggregates are transferred to a serum-free medium, which is DMEM/F-12 medium containing 3 µM CHIR99021 and added with 1× N2 supplement, and cultured until day 21 from the start of the floating culture. At day 21 from the start of the floating culture, the aggregates are dispersed in cell dispersion solution Accutase (ICT), and debris was removed using a 40 µm cell strainer. The resulting cells are suspended in a serum-free medium (200 µl), which is a 1:1 mixture of DMEM/F-12 medium and Neurobasal medium added with 10% KSR, ½ N2 supplement, ½ B27 supplement, 20 µM Y27632, and seeded in a 65 mm Boyden chamber (Transwell, Corning Incorporated) after a coating treatment with SYNTHEMAX™ substrate at $2 \times 10^5$ cells per well, a medium (1 ml) having the same composition is also added to a lower well, and adhesion culture is performed at 37° C., 5% $CO_2$. At day 24 from the start of the floating culture, namely, at day 3 from the start of the adhesion culture, any of 3 µM CHIR99021, 10 µM SU-5402, 1 nM recombinant human BMP4 protein and 50 ng/ml recombinant human activin, or these in combination may be added. The medium is exchanged every 3 days, and the level of epithelial formation is observed under a microscope at day 40 from the start of the floating culture.

In this way, retinal pigment epithelial cell sheet is produced from human iPS cells.

This application is based on a patent application No. 2013-232795 filed in Japan (filing date: Nov. 11, 2013), the contents of which are incorporated in full herein.

INDUSTRIAL APPLICABILITY

According to the production method of the present invention, retinal pigment epithelial cell or retinal pigment epithelial cell sheet can be produced with high efficiency.

The invention claimed is:

1. A method for producing a retinal pigment epithelial cell, comprising
   (1) a first step of subjecting pluripotent stem cells to floating culture in a serum-free medium to form an aggregate of pluripotent stem cells,
   (2) a second step of subjecting the aggregate formed in step (1) to floating culture in a serum-free medium or serum-containing medium each being free of a substance that can enhance signal transduction pathway mediated by Sonic hedgehog and containing a substance that can enhance signal transduction pathway mediated by BMP at a concentration capable of inducing differentiation of cells forming pluripotent stem cell aggregates into retinal cells from day 1 or later from the start of the floating culture in step (1) until a cell expressing Rax gene appears, thereby obtaining an aggregate containing retinal progenitor cells, and
   (3) a third step of subjecting the aggregate obtained in step (2) to floating culture in a serum-free medium or serum-containing medium each being free of a substance that can enhance signal transduction pathway mediated by Sonic hedgehog and a substance that can enhance signal transduction pathway mediated by BMP and containing a substance that can enhance signal transduction pathway mediated by Wnt, thereby obtaining an aggregate containing retinal pigment epithelial cells,
   wherein the substance that can enhance signal transduction pathway mediated by BMP is selected from the group consisting of BMP proteins, BMP2, BMP4, BMP7, GDF proteins, GDF7, anti-BMP receptor antibody, and BMP partial peptide.

2. A method for producing a retinal pigment epithelial cell sheet, comprising
   (1) a first step of subjecting pluripotent stem cells to floating culture in a serum-free medium to form an aggregate of pluripotent stem cells,
   (2) a second step of subjecting the aggregate formed in step (1) to floating culture in a serum-free medium or serum-containing medium each being free of a substance that can enhance signal transduction pathway mediated by Sonic hedgehog and containing a substance that can enhance signal transduction pathway mediated by BMP at a concentration capable of inducing differentiation of cells forming pluripotent stem cell aggregates into retinal cells from day 1 or later from the start of the floating culture in step (1) until a cell expressing Rax gene appears, thereby obtaining an aggregate containing retinal progenitor cells,
   (3) a third step of subjecting the aggregate obtained in step (2) to floating culture in a serum-free medium or serum-containing medium each being free of a substance that can enhance signal transduction pathway mediated by Sonic hedgehog and a substance that can enhance signal transduction pathway mediated by BMP and containing a substance that can enhance signal transduction pathway mediated by Wnt, thereby obtaining an aggregate containing retinal pigment epithelial cells, and
   (4) a fourth step of dispersing the aggregate obtained in step (3) and subjecting the resulting cells to adhesion culture,
   wherein the substance that can enhance signal transduction pathway mediated by BMP is selected from the group consisting of BMP proteins, BMP2, BMP4, BMP7, GDF proteins, GDF7, anti-BMP receptor antibody, and BMP partial peptide.

3. The production method according to claim 2, wherein the adhesion culture is performed in the presence of a serum replacement in said step (4).

4. The production method according to claim 2, wherein the adhesion culture is performed in the presence of a ROCK inhibitory substance, in said step (4).

5. The production method according to claim 2, wherein the adhesion culture is performed in a serum-free medium or serum-containing medium further comprising one or more substances selected from the group consisting of a substance that can enhance signal transduction pathway mediated by Wnt, a substance inhibiting the FGF signal pathway, a substance capable of enhancing a signal mediated by Activin and a substance that can enhance signal transduction pathway mediated by BMP, in said step (4).

6. The production method according to claim 5, wherein the substance inhibiting the FGF signal pathway is selected from the group consisting of FGF receptor, FGF receptor inhibitor, SU-5402, AZD4547, BGJ398, MAP kinase cascade inhibitory substance, MEK inhibitor, MAPK inhibitor, ERK inhibitor, PI3 kinase inhibitor, and Akt inhibitor.

7. The production method according to claim 5, wherein the substance capable of enhancing a signal mediated by Activin is selected from the group consisting of a proteins belonging to the Activin family, Activin A, Activin B, Activin C, Activin AB, Activin receptor, and Activin receptor agonist.

8. The production method according to claim 2, wherein the adhesion culture is performed on a culture vessel material having a surface treated with a culture substrate, in said step (4).

9. The production method according to claim 8, wherein said culture substrate is a synthetic culture substrate.

10. The production method according to claim 8, wherein said culture substrate is laminin.

11. The production method according to claim 1, wherein the pluripotent stem cells are primate pluripotent stem cells.

12. The production method according to claim 1, wherein the pluripotent stem cells are human pluripotent stem cells.

13. The method according to claim 1, wherein the step (1) and step (2) are performed in the presence of a serum replacement.

14. The method according to claim 1, wherein the floating culture is performed in the absence of a basement membrane preparation.

15. The method according to claim 1, wherein the substance that can enhance signal transduction pathway mediated by BMP is one or more proteins selected from the group consisting of BMP2, BMP4, BMP7 and GDF7.

16. The method according to claim 1, wherein the serum-free medium or serum-containing medium each being free of a substance that can enhance signal transduction pathway mediated by Sonic hedgehog and a substance that can enhance signal transduction pathway mediated by BMP and containing a substance that can enhance signal transduction pathway mediated by Wnt in step (3) further comprises a substance inhibiting the FGF signal pathway.

17. The production method according to claim 1, wherein the substance that can enhance signal transduction mediated by Wnt is selected from the group consisting of a protein belonging to Wnt family, Wnt1, Wnt3a, Wnt7a, Wnt receptor agonist, GSK3β inhibitor, 6-Bromoindirubin-3'-oxime (BIO), CHIR99021, and Kenpaullone.

18. The method according to claim 1, wherein the substance that can enhance signal transduction pathway mediated by BMP is added to the medium of step (2) between day 1 and day 15 from the start of the floating culture in step (1).

19. A method of evaluating toxicity or drug efficacy of a test substance, comprising producing a retinal pigment epithelial cell by the method according to claim 1, and bringing the retinal pigment epithelial cell into contact with the test substance, and examining the influence of the substance on the cell or cell sheet.

20. A method of treating a disease due to a disorder of a retinal tissue, comprising producing a retinal pigment epithelial cell by the method according to claim 1, and transplanting an effective amount of the retinal pigment epithelial cell to a subject in need of the transplantation.

\* \* \* \* \*